(12) United States Patent
Constantine et al.

(10) Patent No.: US 11,052,036 B2
(45) Date of Patent: Jul. 6, 2021

(54) COLOURED SURFACTANT COMPOSITION

(71) Applicant: COSMETIC WARRIORS LIMITED, Poole (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB)

(73) Assignee: COSMETIC WARRIORS LIMITED, Poole (GB)

( * ) Notice: Subject to any disclaimer, the term of this patent is extended or adjusted under 35 U.S.C. 154(b) by 56 days.

(21) Appl. No.: 15/757,326

(22) PCT Filed: Sep. 2, 2016

(86) PCT No.: PCT/GB2016/052709
§ 371 (c)(1),
(2) Date: Mar. 2, 2018

(87) PCT Pub. No.: WO2017/037464
PCT Pub. Date: Mar. 9, 2017

(65) Prior Publication Data
US 2018/0235866 A1     Aug. 23, 2018

(30) Foreign Application Priority Data

Sep. 4, 2015 (GB) .................................. 1515734

(51) Int. Cl.
| | |
|---|---|
| *A61K 8/23* | (2006.01) |
| *A61K 8/92* | (2006.01) |
| *A61K 8/46* | (2006.01) |
| *A61Q 19/10* | (2006.01) |
| *A61K 8/02* | (2006.01) |
| *A61K 8/04* | (2006.01) |
| *A61K 8/19* | (2006.01) |
| *A61K 8/41* | (2006.01) |
| *A61K 8/42* | (2006.01) |

(52) U.S. Cl.
CPC .............. *A61K 8/922* (2013.01); *A61K 8/022* (2013.01); *A61K 8/0216* (2013.01); *A61K 8/04* (2013.01); *A61K 8/19* (2013.01); *A61K 8/416* (2013.01); *A61K 8/42* (2013.01); *A61K 8/463* (2013.01); *A61K 8/466* (2013.01); *A61Q 19/10* (2013.01); *A61K 2800/31* (2013.01); *A61K 2800/42* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 6,310,014 B1 * | 10/2001 | Rau ......................... | A61Q 3/00 134/42 |
| 6,551,603 B1 | 4/2003 | Vinski et al. | |
| 6,903,066 B2 * | 6/2005 | Kischkel ................ | C11D 1/662 510/371 |
| 10,188,589 B2 * | 1/2019 | Das ........................ | A61K 8/416 |
| 2003/0003069 A1 | 1/2003 | Carson et al. | |
| 2003/0170301 A1 | 9/2003 | Wehling | |
| 2008/0081776 A1 * | 4/2008 | Crotty ................... | A61K 8/0295 510/130 |
| 2008/0299057 A1 * | 12/2008 | Lin ......................... | A61Q 1/06 424/59 |

FOREIGN PATENT DOCUMENTS

| | | |
|---|---|---|
| CN | 102860950 A | 6/2013 |
| CN | 104224574 A | 12/2014 |
| CN | 105106037 A | 12/2015 |
| EP | 0312668 A1 | 4/1989 |
| JP | H03-74321 A | 3/1991 |
| JP | 2014-109003 A | 6/2014 |
| WO | 2010/094975 A2 | 8/2010 |
| WO | 2015/014667 A1 | 2/2015 |

OTHER PUBLICATIONS

International Search Report and Written Opinion for PCT/GB2016/052709, dated Dec. 6, 2016.
Search Report for British Patent Application No. 1515734.0, dated Jun. 1, 2016.

* cited by examiner

*Primary Examiner* — Susan T Tran
(74) *Attorney, Agent, or Firm* — Merchant & Gould P.C.

(57) ABSTRACT

A colored surfactant composition includes (i) an anhydrous surfactant; (ii) a vegetable oil, a vegetable butter or mixture thereof; and (iii) an oil dispersible water insoluble coloring.

10 Claims, No Drawings

COLOURED SURFACTANT COMPOSITION

This application is a National Stage of PCT/GB2016/052709, filed 2 Sep. 2016, which claims benefit of British Patent Application No. 1515734.0, filed 4 Sep. 2015 which applications are incorporated herein by reference. To the extent appropriate, a claim of priority is made to each of the above disclosed applications.

FIELD OF THE INVENTION

The present invention relates to a surfactant composition for use as a cosmetic, a process for producing said product and products prepared by the method herein.

BACKGROUND TO THE INVENTION

The use of surfactants in personal hygiene and cosmetic products is well known in the art. Surfactants have the ability to modify the interfaces between various phases, resulting in a reduction of the surface tension. This causes a desired effect, such as a cleansing, emulsification, or foaming action.

Whilst the formation of a lather is not essential to the function of a cleansing or bathing composition, it is desirable for the product to have a foaming ability, due to consumer demand. Foam or lather resulting from the reduction in the surface tension of bathing water and the proceeding entrapment of air appears white, translucent or iridescent as a result of visible light reflecting off of, or traversing a mass of congregated soap bubbles. The ability to change and dictate the colour of a lather or foam produced by a surfactant composition is highly desirable, especially with regards to cleansing and bathing compositions, in order to enhance the user experience.

The present invention seeks to provide a surfactant composition that is capable of yielding a lather or foam with substantially uniform coloured bubbles, resulting in an enhanced user experience. The present invention further provides cosmetic compositions and methods of producing coloured lather or foam.

SUMMARY OF THE INVENTION

In a first aspect, there is provided a coloured surfactant composition comprising
(i) an anhydrous surfactant;
(ii) a vegetable oil, a vegetable butter or mixture thereof;
(iii) an oil dispersible water insoluble colouring.

In a second aspect, there is provided a method for preparing coloured surfactant composition as defined herein, the method comprising the steps of:
(a) providing a vegetable oil, a vegetable butter or mixture thereof at a temperature of at least 60° C.;
(b) mixing an oil dispersible water insoluble colouring with the vegetable oil, vegetable butter or mixture thereof to provide a coloured vegetable oil, vegetable butter or mixture thereof; and
(c) mixing the coloured vegetable oil, vegetable butter or mixture thereof and an anhydrous surfactant.

In a third aspect, there is provided a coloured surfactant composition prepared by a method as defined herein.

In a fourth aspect, there is provided a cosmetic composition comprising coloured surfactant composition as defined herein.

In a fifth aspect, there is provided a method of bathing, the method comprising the steps of:

(a) contacting a cosmetic composition as defined herein with water to provide coloured bathing water and foam;
(b) bathing in the coloured bathing water and foam For ease of reference, these and further aspects of the present invention are now discussed under appropriate section headings. However, the teachings under each section are not necessarily limited to each particular section.

Advantages

It has been found that when a surfactant composition, such as a bathing product, is prepared containing or comprising a coloured surfactant composition in accordance with the present invention, the following advantages may be achieved. Firstly, it is possible to create foam on contact of the coloured surfactant composition with water that is coloured. This is particularly desirable for end users who are accustomed to foam which appears white, translucent or iridescent. Furthermore, if the coloured surfactant composition is combined with an additional water soluble colouring, a multicoloured surfactant composition can be formed. In this aspect, a composition is provided which has the ability to colour a body of water one colour, whilst colouring the lather or foam generated by the surfactant another distinct colour.

The use of dyes or pigments in surfactant compositions have traditionally been used to colour cosmetic compositions or to colour a body of water, such as in a bath. Due to simple kinetic theory water soluble dyes and pigments will naturally diffuse from an area of high concentration to an area of lower concentration, until a state of equilibrium has been attained. Because of this, water soluble dyes and pigments are unsuitable for colouring lather or foam, due to their tendency to diffuse from the lather or foam into an area of lower concentration, such as a body of water, resulting in varied or inadequate colouration of the lather or foam.

It has been found that if one attempts to address the issue of diffusion by simple use of an oil dispersible water insoluble colouring, in place of a water soluble dye or pigment, this results in an unpleasant effect. In particular, it is found that the oil dispersible water insoluble colouring simply floats on the surface of the body of water and would not be taken up by the foam. We have found that, in contrast, producing a coloured surfactant, by combining an oil dispersible water insoluble colouring with vegetable oil or butter together with a surfactant component, a coloured lather or foam can be produced, whereby the colouring is dispersed throughout the lather or foam, resulting in a mass of coloured bubbles with a high colour intensity.

DETAILED DESCRIPTION

As discussed herein, the present invention provides a coloured surfactant composition comprising
(i) an anhydrous surfactant;
(ii) a vegetable oil, a vegetable butter or mixture thereof;
(iii) an oil dispersible water insoluble colouring.

Anhydrous Surfactant

The anhydrous surfactant for use in the present invention may be present in any suitable amount. In one aspect the anhydrous surfactant is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt. % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

In one aspect the anhydrous surfactant is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 25 to 65 wt. % based on the coloured surfactant composition, such as in an amount of from 25 to 60 wt % based on the coloured surfactant composition, such as in an amount of from 25 to 55 wt. % based on the coloured surfactant composition, such as in an amount of from 25 to 50 wt. % based on the coloured surfactant composition, such as in an amount of from 25 to 45 wt. % based on the coloured surfactant composition, such as in an amount of from 25 to 40 wt. % based on the coloured surfactant composition, such as in an amount of from 25 to 35 wt. % based on the coloured surfactant composition.

The anhydrous surfactant for use in the present invention may be selected from any suitable anhydrous surfactants. By the term anhydrous it is meant that the surfactant comprises less than 10 wt % water based on the surfactant. In a preferred aspect the anhydrous surfactant comprise less than 5 wt % water based on the surfactant. In a preferred aspect the anhydrous surfactant comprise less than 1 wt % water based on the surfactant. In a preferred aspect the anhydrous surfactant comprise less than 0.1 wt % water based on the surfactant. In a preferred aspect the anhydrous surfactant comprise less than 0.01 wt % water based on the surfactant. In a preferred aspect the anhydrous surfactant comprise less than 0.001 wt % water based on the surfactant.

The anhydrous surfactant is preferably selected from disodium lauryl sulfosuccinate, sodium lauryl sulphate, sodium cocoamphoacetate, sodium laureth sulphate, lauryl betaine, sodium lauroyl sarcosinate, sodium alkyl sulfate, disodium laureth sulfosuccinate, sodium lauryl sulfoacetate, cocamide monoethanolamine, cetrimonium bromide and mixtures thereof.

In one aspect the anhydrous surfactant is selected from disodium lauryl sulfosuccinate, sodium lauryl sulphate, sodium laureth sulphate, and mixtures thereof. In a further preferred aspect the anhydrous surfactant is disodium laureth sulfosuccinate.

The term 'surfactant' is recognised in the art to be a species that is capable of modifying the nature of surfaces and therefore interfaces. It is generally understood that there are 4 main categories of surfactant: cationic, anionic, non-ionic and amphoteric. Anionic surfactants are the most widely used type of surfactants in the cosmetic industry and are known to be amphiphilic, comprising of a hydrophilic group and a lipophilic moiety. Due to the affinity of the surfactant's lipophilic moiety for vegetable oil or butter, a strong interaction can be formed between the surfactant and the vegetable oil or butter and oil dispersible water insoluble colouring, thereby creating the coloured surfactant precursor. When the coloured surfactant is added to water and agitated, foam is produced, whereby the concentration of surfactant in the foam is high. Due to the strong interaction between the surfactant and vegetable oil or butter and oil dispersible water insoluble colouring, the vegetable oil or butter and oil dispersible water insoluble colouring is drawn on to the surface of the foam's bubbles, creating the appearance of coloured lather or foam.

It has been found that if hydrated surfactants are used the vegetable oil or butter and the oil dispersible water insoluble colouring could not be incorporated sufficiently, resulting in the coloured surfactant precursor separating before it could be applied to a cosmetic base. However, it has been found possible to incorporate a relatively small amount of hydrated surfactant into the coloured surfactant composition. An exemplary hydrated surfactant may contain a mixture of water and a surfactant, whereby the solution contains about 70% anionic active matter, such as a 70% active sodium laureth sulphate.

Accordingly, one or more hydrated surfactants may be present in the coloured surfactant composition, where the total amount of hydrated surfactant is 5 wt. % or less based on the coloured surfactant composition. In one aspect, one or more hydrated surfactants may be present in the coloured surfactant composition, where the total amount of hydrated surfactant is 4 wt. % or less based on the coloured surfactant composition. In one aspect, one or more hydrated surfactants may be present in the coloured surfactant composition, where the total amount of hydrated surfactant is 3 wt. % or less based on the coloured surfactant composition. In one aspect, one or more hydrated surfactants may be present in the coloured surfactant composition, where the total amount of hydrated surfactant is 2 wt. % or less based on the coloured surfactant composition.

In one aspect, the coloured surfactant composition is substantially free of hydrated surfactant.

An anhydrous surfactant in either solid or liquid form may be used and results in the desired coloured lather or foam. However we have found that when a powdered anhydrous surfactant with a larger particle size is utilised, the resulting lather or foam does not have the same colour intensity when compared to foam created by a powdered surfactant with a smaller particle size. Thus in a preferred aspect surfactant has a mass median diameter (D50) from 50 to 100 μm. This is found to yield large masses of coloured bubbles.

Vegetable Oil, Vegetable Butter

The vegetable oil, vegetable butter or mixture thereof for use in the present invention may be present in any suitable amount. In one aspect the vegetable oil, vegetable butter or mixture thereof is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt. % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

The vegetable oil or butter for use in the present invention may be selected from any suitable vegetable oil, vegetable butter or mixture thereof. In one aspect the composition comprises one or more vegetable oils. In one aspect the vegetable oil, vegetable butter or mixture thereof is selected from vegetable oils. In one aspect the vegetable oil, vegetable butter or mixture thereof is selected from coconut oil, almond oil, corn oil, jojoba oil, castor oil, olive oil, grape seed oil, argan oil, moringa oil, baobab oil, rose hip oil, kalahari melon oil, brazil nut oil and mixtures thereof. In one aspect the vegetable oil, vegetable butter or mixture thereof is selected from coconut oil, almond oil, moringa oil, olive oil and mixtures thereof.

The vegetable butters used in the present invention are triglycerides, which are found to be solid (including solid-like, discussed above) at normal usage temperatures. For the avoidance of doubt the vegetable butter is a triglyceride which remains substantially solid at up to 30° C. It will be appreciated however that it is not a requirement that the vegetable butter have a solid fat content of 100% at normal usage temperatures. In a preferred aspect the solid fat has a solid fat content of at least 70%, preferably at least 80%, preferably at least 90%, preferably at least 95%, preferably at least 98%, preferably at least 99% at 25° C.

Oil Dispersible Water Insoluble Colouring

As discussed herein the composition contains an oil dispersible water insoluble colouring. By 'water insoluble' it is meant that the colour has a solubility in water of less than 10 mg of colouring per litre of water at 25° C.

By 'oil dispersible' it is meant that the colour may be dissolved in oil or may be dispersed in oil i.e. when mixed in oil it does not form a separate phase.

Water insoluble dyes or pigments commonly used in the cosmetics industry, such as lake pigments, can be rendered insoluble by precipitating a water soluble dye onto an inert and insoluble binder, or mordant, such as metal oxides and metallic salts, inhibiting the ability of dyes or pigments to diffuse into water. Other colourants exist, such as inorganic pigments and oil soluble dyes that are also insoluble in water, but soluble or dispersible in oil. Whilst they are insoluble in water, they can be dispersed within a carrier oil or molten vegetable butter, allowing them to be applied to a wide range of textiles, foodstuffs and cosmetics.

The oil dispersible water insoluble colouring thereof for use in the present invention may be present in any suitable amount. In one aspect the oil dispersible water insoluble colouring is present in an amount of from 0.01 to 5 wt. % based on the coloured surfactant composition, such as in an amount of from 0.01 to 4 wt. % based on the coloured surfactant composition, such as in an amount of from 0.01 to 3 wt. % based on the coloured surfactant composition, such as in an amount of from 0.02 to 3 wt. % based on the coloured surfactant composition, such as in an amount of from 0.03 to 3 wt. % based on the coloured surfactant composition, such as in an amount of from 0.05 to 3 wt. % based on the coloured surfactant composition, such as in an amount of from 0.01 to 2 wt. % based on the coloured surfactant composition, such as in an amount of from 0.01 to 1 wt. % based on the coloured surfactant composition, such as in an amount of from 0.01 to 0.8 wt. % based on the coloured surfactant composition, such as in an amount of from 0.01 to 0.6 wt. % based on the coloured surfactant composition, such as in an amount of from 0.01 to 0.4 wt. % based on the coloured surfactant composition, such as in an amount of from 0.01 to 0.2 wt. % based on the coloured surfactant composition, such as in an amount of from 0.01 to 0.1 wt. % based on the coloured surfactant composition, such as in an amount of from 0.05 to 2 wt. % based on the coloured surfactant composition, such as in an amount of from 0.05 to 1 wt. % based on the coloured surfactant composition, such as in an amount of from 0.05 to 0.8 wt. % based on the coloured surfactant composition, such as in an amount of from 0.05 to 0.6 wt. % based on the coloured surfactant composition, such as in an amount of from 0.05 to 0.4 wt. % based on the coloured surfactant composition, such as in an amount of from 0.05 to 0.2 wt. % based on the coloured surfactant composition, such as in an amount of from 0.05 to 0.1 wt. % based on the coloured surfactant composition.

The oil dispersible water insoluble colouring for use in the present invention may be selected from any suitable oil dispersible water insoluble colouring. In one aspect the oil dispersible water insoluble colouring is selected from lake colours, inorganic pigments, inorganic dyes, water insoluble organic pigments, water insoluble organic dyes and mixtures thereof.

In one aspect the oil dispersible water insoluble colouring is selected from Lake Colours and mixtures thereof. As understood by one skilled in the art, a Lake Colour is a water insoluble pigment comprising a dye precipitated on to an inert binder. The inert binder is often referred to as a "mordant" and is often a metallic salt. Thus in one aspect the oil dispersible water insoluble colouring is selected from water insoluble pigment comprising a dye precipitated on to an inert binder.

Thus in one aspect the oil dispersible water insoluble colouring is selected from water insoluble pigment comprising (i) a dye selected from FD&C Red No 2, FD&C Red No 3, FD&C Red No 40, FD&C Blue No 1, FD&C Blue No 2, FD&C Green No 3, FD&C Yellow No 5, FD&C Yellow No 6, D&C Red No 6, D&C Red No 7, D&C Red No 21, D&C Red No 22, D&C Red No 27, D&C Red No 28, D&C Red No 30, D&C Red No 33, D&C Red No 34, D&C Red No 36, D&C Yellow No 10, D&C Orange No 5 and mixtures thereof;
(ii) precipitated on to an inert binder.

Thus in one aspect the oil dispersible water insoluble colouring is selected from water insoluble pigment comprising (i) a dye selected from FD&C Red No 2, FD&C Red No 3, FD&C Red No 40, FD&C Blue No 1, FD&C Blue No 2, FD&C Green No 3, FD&C Yellow No 5, FD&C Yellow No 6, D&C Red No 6, D&C Red No 7, D&C Red No 21, D&C Red No 22, D&C Red No 27, D&C Red No 28, D&C Red No 30, D&C Red No 33, D&C Red No 34, D&C Red No 36, D&C Yellow No 10, D&C Orange No 5 and mixtures thereof;
(ii) precipitated on to an inert binder selected from salts of aluminium, barium, calcium, potassium, copper, iron, sodium, tin, zinc and mixtures thereof.

In one aspect the oil dispersible water insoluble colouring is selected from water insoluble pigment comprising
(i) a dye selected from FD&C Red No 2, FD&C Red No 3, FD&C Red No 40, FD&C Blue No 1, FD&C Blue No 2, FD&C Green No 3, FD&C Yellow No 5, FD&C Yellow No 6, D&C Red No 6, D&C Red No 7, D&C Red No 21, D&C Red No 22, D&C Red No 27, D&C Red No 28, D&C Red No 30, D&C Red No 33, D&C Red No 34, D&C Red No 36, D&C Yellow No 10, D&C Orange No 5 and mixtures thereof;
(ii) precipitated on to an inert binder selected from aluminium hydroxide, aluminium (III) oxide, barium sulphate, calcium sulphate, aluminium potassium sulphate, aluminium acetate, aluminium sulfate, aluminium ammonium sulfate, copper (II) sulphate, potassium dichromate, iron (II) sulfate, sodium dithionite, tin (IV) chloride, zinc acetate and mixtures thereof.

In one aspect the oil dispersible water insoluble colouring is selected from water insoluble pigment comprising
(i) a dye selected from FD&C Red No 2, FD&C Red No 3, FD&C Red No 40, FD&C Blue No 1, FD&C Blue No 2, FD&C Green No 3, FD&C Yellow No 5, FD&C Yellow No 6, D&C Red No 6, D&C Red No 7, D&C Red No 21, D&C Red No 22, D&C Red No 27, D&C Red No 28, D&C Red No 30, D&C Red No 33, D&C Red No 34, D&C Red No 36, D&C Yellow No 10, D&C Orange No 5 and mixtures thereof;
(ii) precipitated on to an inert binder selected from aluminium hydroxide, aluminium (III) oxide, aluminium sulfate, barium sulphate, calcium sulphate and mixtures thereof.

In one aspect the oil dispersible water insoluble colouring is selected from FD&C Red No 2 Lake, FD&C Red No 3 Lake, FD&C Red No 40 Lake, FD&C Blue No 1 Lake, FD&C Blue No 2 Lake, FD&C Green No 3 Lake, FD&C Yellow No 5 Lake, FD&C Yellow No 6 Lake, D&C Red No 6 Lake, D&C Red No 7 Lake, D&C Red No 21 Lake, D&C Red No 22 Lake, D&C Red No 27 Lake, D&C Red No 28 Lake, D&C Red No 30 Lake, D&C Red No 33 Lake, D&C Red No 34 Lake, D&C Red No 36 Lake, D&C Yellow No 10 Lake, D&C Orange No 5 and mixtures thereof;

In one aspect the oil dispersible water insoluble colouring is selected from D&C Red No. 30 Aluminium Lake, FD&C Blue No 1 Aluminium Lake and mixtures thereof.

As discussed herein, we have found that, in contrast, producing a coloured surfactant, by combining an oil dispersible water insoluble colouring with vegetable oil or butter together with a surfactant component, a coloured lather or foam can be produced, whereby the colouring is dispersed throughout the lather or foam, resulting in a mass of coloured bubbles with a high colour intensity. The term 'uniform', when referred to in conjunction with lather, foam or bubbles, is intended to refer to the uniform colouration of the lather, foam or bubbles, such that the colour intensity is evenly dispersed and does not dissipate over a given period of time. It is intended that the lather, foam or bubbles maintain their colour intensity for the period of time that the bubbles exist.

Method

As discussed herein the present invention provides a method for preparing coloured surfactant composition as described herein, the method comprising the steps of:
(a) providing a vegetable oil, a vegetable butter or mixture thereof at a temperature of at least 60° C.;
(b) mixing an oil dispersible water insoluble colouring with the vegetable oil, vegetable butter or mixture thereof to provide a coloured vegetable oil, vegetable butter or mixture thereof; and
(c) mixing the coloured vegetable oil, vegetable butter or mixture thereof and an anhydrous surfactant.

In the method, in one preferred aspect the anhydrous surfactant is mixed with the coloured vegetable oil, vegetable butter or mixture thereof in an amount to saturate the coloured oil with anhydrous surfactant.

The present invention also provides a product obtained or obtainable by a process as described herein.

Cosmetic Composition

The coloured surfactant composition is typically used as a precursor for the preparation of a cosmetic composition. Thus in a further aspect the present invention provides a cosmetic composition comprising a coloured surfactant composition as described herein.

The cosmetic composition of the present invention may be a solid or a liquid. In one aspect the cosmetic composition is solid.

If the product of the present invention is solid, the shape of the solid products of the present invention is not limited. It may be that the solid products are provided with a shape which would be aesthetically pleasing and/or which aids in the use of the product. For example, it may be that the solid product is produced in such a manner so that it solidifies in a shape which is ergonomically acceptable to the user. Products which are approximately spherical, cuboidal or cylindrical are each envisaged.

The solid products of the present invention are compositions which can substantially sustain their physical shape when unsupported by external means, e.g. packaging etc. Thus, they are considered to be solid, solid-like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

Carbon Dioxide Effervescent Product

In one aspect, the present invention provides a cosmetic composition that effervesces carbon dioxide.

In this aspect, preferably the anhydrous surfactant is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt. % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

In this aspect, preferably the vegetable oil, vegetable butter or mixture thereof is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt. % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

In this aspect, preferably the oil dispersible water insoluble colouring is present in an amount of from 0.01 to 5 wt. % based on the coloured surfactant composition, such as in an amount of from 0.01 to 4 wt. % based on the coloured surfactant composition, such as in an amount of from 0.01 to 3 wt. % based on the coloured surfactant composition, such as in an amount of from 0.02 to 3 wt. % based on the coloured surfactant composition, such as in an amount of from 0.03 to 3 wt. % based on the coloured surfactant composition, such as in an amount of from 0.05 to 3 wt. % based on the coloured surfactant composition, such as in an amount of from 0.01 to 2 wt. % based on the coloured surfactant composition, such as in an amount of from 0.01 to 1 wt. % based on the coloured surfactant composition, such as in an amount of from 0.01 to 0.8 wt. % based on the coloured surfactant composition, such as in an amount of from 0.01 to 0.6 wt. % based on the coloured surfactant composition, such as in an amount of from 0.01 to 0.4 wt. % based on the coloured surfactant composition, such as in an amount of from 0.01 to 0.2 wt. % based on the coloured surfactant composition, such as in an amount of from 0.01 to 0.1 wt. % based on the coloured surfactant composition, such as in an amount of from 0.05 to 2 wt. % based on the coloured surfactant composition, such as in an amount of from 0.05 to 1 wt. % based on the coloured surfactant composition, such as in an amount of from 0.05 to 0.8 wt. % based on the coloured surfactant composition, such as in an amount of from 0.05 to 0.6 wt. % based on the coloured surfactant composition, such as in an amount of from 0.05 to 0.4 wt. % based on the coloured surfactant composition, such as in an amount of from 0.05 to 0.2 wt. % based on the coloured surfactant composition, such as in an amount of from 0.05 to 0.1 wt. % based on the coloured surfactant composition.

In one aspect, if present, the total amount of hydrated surfactant in the cosmetic composition is 2 wt. % or less based on the cosmetic composition. In one aspect, the total amount of hydrated surfactant in the cosmetic composition is 1.5 wt. % or less based on the cosmetic composition. In one aspect, the total amount of hydrated surfactant in the cosmetic composition is 1 wt. % or less based on the cosmetic composition. In one aspect, the cosmetic composition is substantially free of hydrated surfactant.

Thus in a further broad aspect, the present invention provides
a cosmetic composition comprising
(a) coloured surfactant component, wherein the coloured surfactant component comprises
  (i) an anhydrous surfactant present in an amount of from 25 to 70 wt. % based on the coloured surfactant composition;
  (ii) a vegetable oil, a vegetable butter or mixture thereof present in an amount of from 25 to 75 wt. % based on the coloured surfactant composition;
  (iii) an oil dispersible water insoluble colouring present in an amount of from 0.01 to 5 wt. % based on the coloured surfactant composition;
(b) a salt of carbonic acid; and
(c) an acidifying agent;
wherein (b) and (c) combine on contact with water to effervesce carbon dioxide.

In one aspect, the above composition comprising (a) the coloured surfactant component, (b) a salt of carbonic acid; and (c) an acidifying agent is in the form of a powder. The powder may be used directly by application to the skin or hair to wash the same. In this manner a 'dry' shower or bathing product may be provided which can be applied to the body or hair in place of a more typical liquid based gel or shampoo. In this manner, the transport and packaging of the material can be reduced.

In one aspect, the powder product containing (a) the coloured surfactant component, (b) a salt of carbonic acid; and (c) an acidifying agent may further comprise a granular exfoliant. In one embodiment, the granular exfoliant is selected from the group consisting of cosmetically acceptable sugar, salt, seeds, sand, clay, ground nuts, ground shell, pumice and mixtures thereof.

In one aspect, the powder product containing (a) the coloured surfactant component, (b) a salt of carbonic acid; and (c) an acidifying agent may further comprise a cosmetically acceptable clays. Preferably the cosmetically acceptable clay is selected from kaolin, calamine, smectite clay and mixtures thereof.

In one aspect, the above composition comprising (a) the coloured surfactant component, (b) a salt of carbonic acid; and (c) an acidifying agent is in solid form. In this aspect the components may be combined and then pressed to form a bath bomb type product. Bath Bomb® or Ballistic® are products primarily designed to provide an experience for the user. They contain sodium bicarbonate and citric acid such that on contact with water they effervesce carbon dioxide. This effervescence provides a pleasant sensation for the user. The products also typically contain oils and/or fragrances which are liberated with the effervescence. This liberation adds to the sensory experience of the user. The provision of the present system further enhances the pleasant sensation for the user by providing coloured foam in the manner described herein.

The a salt of carbonic acid; and an acidifying agent together provide a carbon dioxide effervescent component comprises The salt of carbonic acid and the acidifying agent are present in any suitable amounts to achieve effervescence. One skilled in the art is able to combine these materials to provide the desired rate of effervescence.

Preferably the salt of carbonic acid and the acidifying agent are present in a weight ratio of from 95:5 to 50:50, preferably in a weight ratio of from 90:10 to 50:50, preferably in a weight ratio of from 90:10 to 55:45, preferably in a weight ratio of from 90:10 to 60:40, preferably in a weight ratio of from 90:10 to 70:30.

In one aspect the carbon dioxide effervescent component comprises a salt of carbonic acid selected from alkali metal carbonates, alkali metal bicarbonates and mixtures thereof. Preferably, the salt of carbonic acid is selected from sodium bicarbonate, sodium carbonate and mixtures thereof.

In a preferred aspect the carbon dioxide effervescent component comprises the salt of carbonic acid, and preferably sodium bicarbonate, in an amount of from 40 to 95 wt. % based on the carbon dioxide effervescent component. In a preferred aspect the carbon dioxide effervescent component comprises the salt of carbonic acid, and preferably sodium bicarbonate, in an amount of from 45 to 95 wt. % based on the carbon dioxide effervescent component. In a preferred aspect the carbon dioxide effervescent component comprises the salt of carbonic acid, and preferably sodium bicarbonate, in an amount of from 50 to 95 wt. % based on the carbon dioxide effervescent component. In a preferred aspect the carbon dioxide effervescent component comprises the salt of carbonic acid, and preferably sodium bicarbonate, in an amount of from 50 to 90 wt. % based on the carbon dioxide effervescent component. In a preferred aspect the carbon dioxide effervescent component comprises the salt of carbonic acid, and preferably sodium bicarbonate, in an amount of from 55 to 90 wt. % based on the carbon dioxide effervescent component. In a preferred aspect the carbon dioxide effervescent component comprises the salt of carbonic acid, and preferably sodium bicarbonate, in an amount of from 60 to 85 wt. % based on the carbon dioxide effervescent component. In a preferred aspect the carbon dioxide effervescent component comprises the salt of carbonic acid, and preferably sodium bicarbonate, in an amount of from 60 to 80 wt. % based on the carbon dioxide effervescent component. In a preferred aspect the carbon dioxide effervescent component comprises the salt of carbonic acid, and preferably sodium bicarbonate, in an amount of from 60 to 75 wt. % based on the carbon dioxide effervescent component.

In one aspect the acidifying agent is selected from monocarboxylic acids, dicarboxylic acids, tricarboxylic acids and mixtures thereof.

Preferably the acidifying agent is selected form citric acid, potassium bitartrate (cream of tartar) and mixtures thereof.

In a preferred aspect the carbon dioxide effervescent component comprises the acidifying agent, and preferably citric acid, in an amount of from 5 to 60 wt. % based on the carbon dioxide effervescent component. In a preferred aspect the carbon dioxide effervescent component comprises the acidifying agent, and preferably citric acid, in an amount of from 5 to 55 wt. % based on the carbon dioxide effervescent component. In a preferred aspect the carbon dioxide effervescent component comprises the acidifying agent, and preferably citric acid, in an amount of from 5 to 50 wt. % based on the carbon dioxide effervescent component. In a preferred aspect the carbon dioxide effervescent component comprises the acidifying agent, and preferably citric acid, in an amount of from 5 to 45 wt. % based on the carbon dioxide effervescent component. In a preferred aspect the carbon dioxide effervescent component comprises the acidifying agent, and preferably citric acid, in an amount of from 5 to 40 wt. % based on the carbon dioxide effervescent component. In a preferred aspect the carbon dioxide effervescent component comprises the acidifying agent, and preferably citric acid, in an amount of from 5 to 35 wt. % based on the carbon dioxide effervescent component. In a preferred aspect the carbon dioxide effervescent component comprises the acidifying agent, and preferably citric acid, in an amount of from 5 to 30 wt. % based on the carbon dioxide effervescent component.

In a preferred aspect the carbon dioxide effervescent component comprises sodium bicarbonate in an amount of from 55 to 90 wt. % and citric acid in an amount of from 5 to 40 wt. % based on the carbon dioxide effervescent component.

In one aspect, in the cosmetic composition the (a) coloured surfactant component is present in an amount of from 5 to 50 wt. % based on the cosmetic composition, such as in an amount of from 5 to 45 wt. % based on the cosmetic composition, such as in an amount of from 5 to 40 wt. % based on the cosmetic composition, such as in an amount of from 5 to 35 wt. % based on the cosmetic composition, such as in an amount of from 10 to 35 wt. % based on the cosmetic composition, such as in an amount of from 10 to 30 wt. % based on the cosmetic composition, such as in an amount of from 15 to 25 wt. % based on the cosmetic composition.

In one aspect, in the cosmetic composition the carbon dioxide effervescent component, namely the combined (b) salt of carbonic acid; and (c) acidifying agent, is present in an amount of from 50 to 95 wt. % based on the cosmetic composition, such as in an amount of from 55 to 95 wt. % based on the cosmetic composition, such as in an amount of from 60 to 95 wt. % based on the cosmetic composition, such as in an amount of from 65 to 95 wt. % based on the cosmetic composition, such as in an amount of from 65 to 90 wt. % based on the cosmetic composition, such as in an amount of from 70 to 90 wt. % based on the cosmetic composition, such as in an amount of from 70 to 80 wt. % based on the cosmetic composition.

Solid Bubble Bar

In one aspect, the present invention provides a cosmetic composition that is a 'bubble bar'. It is understood by one skilled in the art that a 'bubble bar' is a solid cosmetic composition which on contact with water, and in particular running water, can be used to generate foam.

In this aspect, preferably the anhydrous surfactant is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 25 to 65 wt. % based on the coloured surfactant composition, such as in an amount of from 25 to 60 wt. % based on the coloured surfactant composition, such as in an amount of from 25 to 55 wt. % based on the coloured surfactant composition, such as in an amount of from 25 to 50 wt. % based on the coloured surfactant composition, such as in an amount of from 25 to 45 wt. % based on the coloured surfactant composition, such as in an amount of from 25 to 40 wt. % based on the coloured surfactant composition, such as in an amount of from 25 to 35 wt. % based on the coloured surfactant composition.

In this aspect, preferably the vegetable oil, vegetable butter or mixture thereof for use in the present invention may be present in any suitable amount. In one aspect the vegetable oil, vegetable butter or mixture thereof is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt. % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

In this aspect, preferably the oil dispersible water insoluble colouring is present in an amount of from 0.01 to 5 wt. % based on the coloured surfactant composition, such as in an amount of from 0.01 to 4 wt. % based on the coloured surfactant composition, such as in an amount of from 0.01 to 3 wt. % based on the coloured surfactant composition, such as in an amount of from 0.02 to 3 wt. % based on the coloured surfactant composition, such as in an amount of from 0.03 to 3 wt. % based on the coloured surfactant composition, such as in an amount of from 0.05 to 3 wt. % based on the coloured surfactant composition, such as in an amount of from 0.01 to 2 wt. % based on the coloured surfactant composition, such as in an amount of from 0.01 to 1 wt. % based on the coloured surfactant composition, such as in an amount of from 0.01 to 0.8 wt. % based on the coloured surfactant composition, such as in an amount of from 0.01 to 0.6 wt. % based on the coloured surfactant composition, such as in an amount of from 0.01 to 0.4 wt. % based on the coloured surfactant composition, such as in an amount of from 0.01 to 0.2 wt. % based on the coloured surfactant composition, such as in an amount of from 0.01 to 0.1 wt. % based on the coloured surfactant composition, such as in an amount of from 0.05 to 2 wt. % based on the coloured surfactant composition, such as in an amount of from 0.05 to 1 wt. % based on the coloured surfactant composition, such as in an amount of from 0.05 to 0.8 wt. % based on the coloured surfactant composition, such as in an amount of from 0.05 to 0.6 wt. % based on the coloured surfactant composition, such as in an amount of from 0.05 to 0.4 wt. % based on the coloured surfactant composition, such as in an amount of from 0.05 to 0.2 wt. % based on the coloured surfactant composition, such as in an amount of from 0.05 to 0.1 wt. % based on the coloured surfactant composition.

In one aspect, if present, the total amount of hydrated surfactant in the cosmetic composition is 2 wt. % or less based on the cosmetic composition. In one aspect, the total amount of hydrated surfactant in the cosmetic composition is 1.5 wt. % or less based on the cosmetic composition. In one aspect, the total amount of hydrated surfactant in the cosmetic composition is 1 wt. % or less based on the cosmetic composition. In one aspect, the cosmetic composition is substantially free of hydrated surfactant.

Thus in a further broad aspect, the present invention provides
a solid cosmetic composition comprising
(a) coloured surfactant component, wherein the coloured surfactant component comprises
  (i) an anhydrous surfactant present in an amount of from 25 to 70 wt. % based on the coloured surfactant composition;
  (ii) a vegetable oil, a vegetable butter or mixture thereof present in an amount of from 25 to 75 wt. % based on the coloured surfactant composition;
  (iii) an oil dispersible water insoluble colouring present in an amount of from 0.01 to 5 wt. % based on the coloured surfactant composition;
(b) sodium bicarbonate, sodium carbonate or a mixture thereof; and
(c) tartaric acid or a salt thereof.

In one aspect, the solid cosmetic composition comprises at least sodium bicarbonate. In one aspect, the solid cosmetic composition comprises at least sodium carbonate. In one aspect, the solid cosmetic composition comprises sodium bicarbonate and sodium carbonate.

In one aspect, the solid cosmetic composition comprises at least tartaric acid. In one aspect, the solid cosmetic composition comprises at least a salt tartaric acid.

The salt of tartaric acid may be any suitable salt. In one aspect the salt is selected from sodium and potassium salts of tartaric acid. In one preferred aspect, the salt is a potassium salt of tartaric acid.

As will be understood by one skilled in the art, tartaric acid is also known as 2,3-dihydroxybutanedioic acid and either a mono salt or a di salt may be formed. In one aspect, the present composition contains a mono salt of tartaric acid. In one preferred aspect, the composition comprises the mono potassium salt of tartaric acid, also known as cream of tartar. Cream of tartar is also known as potassium bitartrate or potassium hydrogen tartrate.

Thus in a further preferred aspect, the present invention provides a solid cosmetic composition comprising
(a) coloured surfactant component, wherein the coloured surfactant component comprises
  (i) an anhydrous surfactant present in an amount of from 25 to 70 wt. % based on the coloured surfactant composition;
  (ii) a vegetable oil, a vegetable butter or mixture thereof present in an amount of from 25 to 75 wt. % based on the coloured surfactant composition;
  (iii) an oil dispersible water insoluble colouring present in an amount of from 0.01 to 5 wt. % based on the coloured surfactant composition;
(b) sodium bicarbonate, optionally sodium carbonate; and
(c) cream of tartar.

In one aspect, in the cosmetic composition the (a) coloured surfactant component is present in an amount of from 5 to 50 wt. % based on the cosmetic composition, such as in an amount of from 5 to 45 wt. % based on the cosmetic composition, such as in an amount of from 5 to 40 wt. % based on the cosmetic composition, such as in an amount of from 5 to 35 wt. % based on the cosmetic composition, such as in an amount of from 10 to 35 wt. % based on the cosmetic composition, such as in an amount of from 10 to 30 wt. % based on the cosmetic composition, such as in an amount of from 15 to 25 wt. % based on the cosmetic composition.

In one aspect, in the cosmetic composition the sodium bicarbonate is present in an amount of from 25 to 75 wt % based on the cosmetic composition, such as in an amount of from 25 to 70 wt. % based on the cosmetic composition, such as in an amount of from 30 to 70 wt. % based on the cosmetic composition, such as in an amount of from 30 to 65 wt. % based on the cosmetic composition, such as in an amount of from 35 to 65 wt. % based on the cosmetic composition, such as in an amount of from 35 to 60 wt. % based on the cosmetic composition, such as in an amount of from 40 to 60 wt. % based on the cosmetic composition, such as in an amount of from 45 to 55 wt. % based on the cosmetic composition.

In one aspect, in the cosmetic composition the tartaric acid or a salt thereof is present in an amount of from 5 to 50 wt. % based on the cosmetic composition, such as in an amount of from 5 to 45 wt % based on the cosmetic composition, such as in an amount of from 5 to 40 wt. % based on the cosmetic composition, such as in an amount of from 5 to 35 wt. % based on the cosmetic composition, such as in an amount of from 10 to 35 wt. % based on the cosmetic composition, such as in an amount of from 10 to 30 wt. % based on the cosmetic composition, such as in an amount of from 15 to 25 wt. % based on the cosmetic composition.

Liquid Bubble Bath

In one aspect, the present invention provides a cosmetic composition that is an oil based bubble bath. It is understood by one skilled in the art that a liquid cosmetic composition, the majority of which is oil, which on contact with water, and in particular running water, can be used to generate foam.

In this aspect, preferably the anhydrous surfactant is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 25 to 65 wt. % based on the coloured surfactant composition, such as in an amount of from 25 to 60 wt. % based on the coloured surfactant composition, such as in an amount of from 25 to 55 wt. % based on the coloured surfactant composition, such as in an amount of from 25 to 50 wt. % based on the coloured surfactant composition, such as in an amount of from 25 to 45 wt. % based on the coloured surfactant composition, such as in an amount of from 25 to 40 wt. % based on the coloured surfactant composition, such as in an amount of from 25 to 35 wt. % based on the coloured surfactant composition.

In this aspect, preferably the vegetable oil, vegetable butter or mixture thereof is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

In this aspect, preferably the oil dispersible water insoluble colouring is present in an amount of from 0.01 to 5 wt. % based on the coloured surfactant composition, such as in an amount of from 0.01 to 4 wt. % based on the coloured surfactant composition, such as in an amount of from 0.01 to 3 wt. % based on the coloured surfactant composition, such as in an amount of from 0.02 to 3 wt. % based on the coloured surfactant composition, such as in an amount of from 0.03 to 3 wt. % based on the coloured surfactant composition, such as in an amount of from 0.05 to 3 wt. % based on the coloured surfactant composition, such as in an amount of from 0.01 to 2 wt. % based on the coloured surfactant composition, such as in an amount of from 0.01 to 1 wt. % based on the coloured surfactant composition, such as in an amount of from 0.01 to 0.8 wt. % based on the coloured surfactant composition, such as in an amount of from 0.01 to 0.6 wt. % based on the coloured surfactant composition, such as in an amount of from 0.01 to 0.4 wt. % based on the coloured surfactant composition, such as in an amount of from 0.01 to 0.2 wt. % based on the coloured surfactant composition, such as in an amount of from 0.01 to 0.1 wt. % based on the coloured surfactant composition, such as in an amount of from 0.05 to 2 wt. % based on the coloured surfactant composition, such as in an amount of from 0.05 to 1 wt. % based on the coloured surfactant composition, such as in an amount of from 0.05 to 0.8 wt. % based on the coloured surfactant composition, such as in an amount of from 0.05 to 0.6 wt. % based on the coloured surfactant composition, such as in an amount of from 0.05 to 0.4 wt. % based on the coloured surfactant composition, such as in an amount of from 0.05 to 0.2 wt. % based on the coloured surfactant composition, such as in an amount of from 0.05 to 0.1 wt. % based on the coloured surfactant composition.

In one aspect, if present, the total amount of hydrated surfactant in the cosmetic composition is 2 wt. % or less based on the cosmetic composition. In one aspect, the total amount of hydrated surfactant in the cosmetic composition is 1.5 wt. % or less based on the cosmetic composition. In one aspect, the total amount of hydrated surfactant in the cosmetic composition is 1 wt. % or less based on the cosmetic composition. In one aspect, the cosmetic composition is substantially free of hydrated surfactant.

Thus in a further broad aspect, the present invention provides a liquid cosmetic composition comprising
(a) coloured surfactant component, wherein the coloured surfactant component comprises
  (i) an anhydrous surfactant present in an amount of from 25 to 70 wt. % based on the coloured surfactant composition;
  (ii) a vegetable oil, a vegetable butter or mixture thereof present in an amount of from 25 to 75 wt. % based on the coloured surfactant composition;
  (iii) an oil dispersible water insoluble colouring present in an amount of from 0.01 to 5 wt. % based on the coloured surfactant composition;
(b) a liquid vegetable oil, wherein the liquid vegetable oil is present in an amount of at least 50 wt % based on the liquid cosmetic composition.

In one aspect, in the cosmetic composition the (a) coloured surfactant component is present in an amount of from 5 to 50 wt. % based on the cosmetic composition, such as in an amount of from 5 to 45 wt. % based on the cosmetic composition, such as in an amount of from 5 to 40 wt. % based on the cosmetic composition, such as in an amount of from 5 to 35 wt. % based on the cosmetic composition, such as in an amount of from 10 to 35 wt. % based on the cosmetic composition, such as in an amount of from 15 to 35 wt. % based on the cosmetic composition, such as in an amount of from 20 to 35 wt. % based on the cosmetic composition, such as in an amount of from 25 to 35 wt. % based on the cosmetic composition.

In one aspect, in the cosmetic composition the (b) a liquid vegetable oil is present in an amount of at least 55 wt % based on the liquid cosmetic composition, such as in an amount of at least 60 wt % based on the cosmetic composition, such as in an amount of at least 65 wt. % based on the cosmetic composition.

In one aspect, in the cosmetic composition the (b) a liquid vegetable oil is present in an amount of from 50 to 90 wt. % based on the cosmetic composition, such as in an amount of from 50 to 85 wt. % based on the cosmetic composition, such as in an amount of from 50 to 80 wt. % based on the cosmetic composition, such as in an amount of from 50 to 75 wt. % based on the cosmetic composition, such as in an amount of from 55 to 75 wt. % based on the cosmetic composition, such as in an amount of from 60 to 75 wt. % based on the cosmetic composition, such as in an amount of from 60 to 70 wt. % based on the cosmetic composition.

Solid Bath Oil

In one aspect, the present invention provides a cosmetic composition that is a solid bath oil. It is understood by one skilled in the art that such a product is an oil based product formulated to hold its form and not readily melt prior to use.

In this aspect, preferably the anhydrous surfactant is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 25 to 65 wt. % based on the coloured surfactant composition, such as in an amount of from 25 to 60 wt. % based on the coloured surfactant composition, such as in an amount of from 25 to 55 wt. % based on the coloured surfactant composition, such as in an amount of from 25 to 50 wt. % based on the coloured surfactant composition, such as in an amount of from 25 to 45 wt. % based on the coloured surfactant composition, such as in an amount of from 25 to 40 wt. % based on the coloured surfactant composition, such as in an amount of from 25 to 35 wt. % based on the coloured surfactant composition.

In this aspect, preferably the vegetable oil, vegetable butter or mixture thereof is present in an amount of from 25 to 80 wt. % based on the coloured surfactant composition, such as in an amount of from 25 to 75 wt. % based on the coloured surfactant composition, such as in an amount of from 25 to 70 wt. % based on the coloured surfactant composition, such as in an amount of from 30 to 70 wt. % based on the coloured surfactant composition, such as in an amount of from 35 to 70 wt. % based on the coloured surfactant composition, such as in an amount of from 40 to 70 wt. % based on the coloured surfactant composition, such as in an amount of from 45 to 70 wt. % based on the coloured surfactant composition, such as in an amount of from 50 to 70 wt. % based on the coloured surfactant composition, such as in an amount of from 45 to 65 wt. % based on the coloured surfactant composition, such as in an amount of from 45 to 60 wt. % based on the coloured surfactant composition.

In this aspect, preferably the oil dispersible water insoluble colouring is present in an amount of from 0.01 to 5 wt. % based on the coloured surfactant composition, such as in an amount of from 0.01 to 4 wt % based on the coloured surfactant composition, such as in an amount of from 0.01 to 3 wt. % based on the coloured surfactant composition, such as in an amount of from 0.02 to 3 wt. % based on the coloured surfactant composition, such as in an amount of from 0.03 to 3 wt. % based on the coloured surfactant composition, such as in an amount of from 0.05 to 3 wt. % based on the coloured surfactant composition, such as in an amount of from 0.01 to 2 wt. % based on the coloured surfactant composition, such as in an amount of from 0.01 to 1 wt. % based on the coloured surfactant composition, such as in an amount of from 0.01 to 0.8 wt. % based on the coloured surfactant composition, such as in an amount of from 0.01 to 0.6 wt. % based on the coloured surfactant composition, such as in an amount of from 0.01 to 0.4 wt. % based on the coloured surfactant composition, such as in an amount of from 0.01 to 0.2 wt. % based on the coloured surfactant composition, such as in an amount of from 0.01 to 0.1 wt. % based on the coloured surfactant composition, such as in an amount of from 0.05 to 2 wt. % based on the coloured surfactant composition, such as in an amount of from 0.05 to 1 wt. % based on the coloured surfactant composition, such as in an amount of from 0.05 to 0.8 wt % based on the coloured surfactant composition, such as in an amount of from 0.05 to 0.6 wt. % based on the coloured surfactant composition, such as in an amount of from 0.05 to 0.4 wt. % based on the coloured surfactant composition, such as in an amount of from 0.05 to 0.2 wt. % based on the coloured surfactant composition, such as in an amount of from 0.05 to 0.1 wt. % based on the coloured surfactant composition.

In one aspect, if present, the total amount of hydrated surfactant in the cosmetic composition is 2 wt. % or less based on the cosmetic composition. In one aspect, the total amount of hydrated surfactant in the cosmetic composition is 1.5 wt. % or less based on the cosmetic composition. In one aspect, the total amount of hydrated surfactant in the cosmetic composition is 1 wt. % or less based on the cosmetic composition. In one aspect, the cosmetic composition is substantially free of hydrated surfactant.

Thus in a further broad aspect, the present invention provides a solid composition comprising
(a) coloured surfactant component, wherein the coloured surfactant component comprises
  (i) an anhydrous surfactant present in an amount of from 25 to 70 wt. % based on the coloured surfactant composition;
  (ii) a vegetable oil, a vegetable butter or mixture thereof present in an amount of from 25 to 75 wt. % based on the coloured surfactant composition;
  (iii) an oil dispersible water insoluble colouring present in an amount of from 0.01 to 5 wt. % based on the coloured surfactant composition;

(b) a hard vegetable butter, wherein the hard vegetable butter is present in an amount of at least 30 wt % based on the solid cosmetic composition.

It is understood by one skilled in the art that a hard vegetable butter is one containing a high saturated fat content and which therefore has a high solid fat content at room temperature.

In one aspect the hard vegetable butter is present in an amount of at least 35 wt % based on the solid cosmetic composition. In one aspect the hard vegetable butter is present in an amount of at least 40 wt % based on the solid cosmetic composition. In one aspect the hard vegetable butter is present in an amount of at least 45 wt % based on the solid cosmetic composition.

In one aspect the hard vegetable butter is present in an amount of from 30 to 80 wt % based on the solid cosmetic composition. In one aspect the hard vegetable butter is present in an amount of from 30 to 70 wt % based on the solid cosmetic composition. In one aspect the hard vegetable butter is present in an amount of from 35 to 65 wt % based on the solid cosmetic composition. In one aspect the hard vegetable butter is present in an amount of from 40 to 60 wt % based on the solid cosmetic composition. In one aspect the hard vegetable butter is present in an amount of from 45 to 55 wt % based on the solid cosmetic composition.

Preferred hard vegetable butters for use in accordance with the present invention may be selected from Cocoa butter, Illipe butter, Murumuru butter, Kokum butter and mixtures thereof.

In one aspect, the composition further comprises a "soft" vegetable butter. It is understood by one skilled in the art that a soft vegetable butter is one containing a high unsaturated fat content in which therefore has a low solid fat content at room temperature.

In one aspect the soft vegetable butter is present in an amount of no greater than 20 wt % based on the solid cosmetic composition. In one aspect the hard vegetable butter is present in an amount of no greater than 15 wt % based on the solid cosmetic composition. In one aspect the hard vegetable butter is present in an amount of no greater than 10 wt % based on the solid cosmetic composition.

Preferred soft vegetable butters for use in accordance with the present invention may be selected from Aloe butter, Avocado butter, Cupuacu butter, Macadamia Nut butter, Mango butter, Olive butter, Shea butter, Coconut butter, Pumpkin Seed butter, Peanut butter, Almond butter and mixtures thereof.

Preferably the hard vegetable butter and soft vegetable butter are present in a weight ratio of from 95:5 to 5:95, preferably in a weight ratio of from 85:15 to 15:85, preferably in a weight ratio of from 75:25 to 25:75, preferably in a weight ratio of from 65:35 to 35:65, preferably in a weight ratio of from 55:45 to 45:55, preferably in a weight ratio of from 75:25 to 65:35.

Preferably the hard vegetable butter and soft vegetable butter are present in a weight ratio of from 95:5 to 65:35, preferably in a weight ratio of from 85:15 to 75:25. As will be understood by those skilled in the art, the greater the proportion of hard vegetable butter present in the composition the drier it will feel. Drier feeling mixtures of butters are better for areas of the body that are prone to increased perspiration, such as feet and hands.

Compositions with increased soft butters feel lighter on the skin, but may produce an increasingly greasy feeling.

In one aspect, in the cosmetic composition the (a) coloured surfactant component is present in an amount of from 30 to 80 wt. % based on the cosmetic composition, such as in an amount of from 30 to 70 wt. % based on the cosmetic composition, such as in an amount of from 35 to 65 wt. % based on the cosmetic composition, such as in an amount of from 35 to 60 wt. % based on the cosmetic composition, such as in an amount of from 40 to 60 wt. % based on the cosmetic composition, such as in an amount of from 40 to 55 wt. % based on the cosmetic composition, such as in an amount of from 45 to 55 wt. % based on the cosmetic composition.

Further Components

The solid product of the present invention may further comprises a water soluble colouring. It has been found that when a surfactant composition comprised of a coloured surfactant composition in accordance with the present invention is combined with an additional water soluble colouring, a multicoloured surfactant composition can be formed. This resulted in the ability to colour a body of water one colour, whilst colouring the lather or foam generated by the surfactant another distinct colour.

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, fragrances, decorative items and mixtures thereof.

It is particularly preferred that the composition of the present invention further comprises a fragrance. Preferably the fragrance is selected from essential oils. Preferably the fragrance, and more preferably the essential oil, is present in an amount of from 0.001 to 10 wt. % based on the cosmetic composition. Preferably the fragrance, and more preferably the essential oil, is present in the cosmetic composition in an amount of from 0.001 to 8 wt. % based on the cosmetic composition. Preferably the fragrance, and more preferably the essential oil, is present in the cosmetic composition in an amount of from 0.001 to 6 wt. % based on the cosmetic composition. Preferably the fragrance, and more preferably the essential oil, is present in the cosmetic composition in an amount of from 1 to 6 wt. % based on the cosmetic composition. Preferably the fragrance, and more preferably the essential oil, is present in the cosmetic composition in an amount of from 4 to about 6 wt. % based on the cosmetic composition.

Fruit and herb extracts and juices, vegetable oils and essential oils are all compatible with the composition.

In one embodiment, the cosmetically acceptable additives are selected from the group consisting of essential oils, vitamins, fragrances, colourings, clays, decorative articles, and mixtures thereof.

The essential oils may be selected based on the fragrance desired, skin type to be treated and other effects desired based on the well-known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients in the present invention do not require cosmetic preservatives. The use of cosmetic preservatives can increase the potential to irritate the skin.

The decorative items which may be present in the solid product include items such as glitter, paper such as rice paper, sequins, dried or fresh flowers, herbs, vegetables, parts thereof or mixtures thereof. Other enhancing materials may also be incorporated.

Further preferred additive materials include vegetable oils, chocolate, herbs and spices, cosmetic colours (e.g. paprika, gardenia extract, D&C red no. 30), beans (e.g. aduki), fruit, fresh or dried (e.g. banana, avocado, mango, papaya, kiwi, raspberry, strawberry, blueberries, grapes, tomato, asparagus, or cucumber), honey, glycerin, cosmetic glitter, other vegetable butters (e.g. mango, avocado), clays (e.g. kaolin), starches (e.g. corn starch), popping candy, lycopodium powder and mixtures thereof.

The above ranges provide preferred amounts of each of the components. Each of these ranges may be taken alone or combined with one or more other component ranges to provide a preferred aspect of the invention.

Cosmetic Method

In a further aspect, the present invention provides a method of bathing, the method comprising the steps of:
(a) contacting a cosmetic composition as defined herein with water to provide coloured bathing water and foam;
(b) bathing in the coloured bathing water and foam.

In a further aspect, the present invention provides a method of generating coloured lather or foam. The first method comprises the steps of (i) applying the surfactant composition to bathing water (ii) agitating the water to generate coloured foam. The second method comprises the steps of (i) applying the surfactant composition directly to the skin (ii) applying water (iii) agitating the surfactant composition in the presence of water directly on the skin to generate a lather or foam.

In one aspect of the present invention, there is provided a method comprising contacting the skin of a user with water in which the solid cosmetic composition as defined herein has been placed in, or has dissolved in, or in which the solid cosmetic composition as defined herein is dissolving. In a typical method, water is run in to the bath at an acceptable temperature. The user immerses their body in the water and the solid cosmetic composition is dropped into the water. The user then watches the effect of the product on the surface of the water as the product dissolves and disperses its colouring, whilst releasing the components. The colouring is thus dispersed through the water. The user then bathes in the water.

EXAMPLE

The invention will now be described with reference to the following non-limiting examples.

General Method

A coloured surfactant composition in accordance with the present invention may be prepared in accordance with the following process:
1. Vegetable oil or butter is heated to 75° C.;
2. Oil dispersible water insoluble colouring is added to the vegetable oil or butter, ensuring the colourant is thoroughly dispersed;
3. Anhydrous surfactant is then incorporated into the vegetable oil or butter and colour mixture.

The coloured surfactant composition can be added to a wide range of cosmetically acceptable bases for a number of reasons, such as: ease of use, reduction in packaging, heightened user experience and suitable dosing of surfactant.

Example 1—Coloured Surfactant Composition

| Material | Weight (g) | wt. % |
|---|---|---|
| Disodium Lauryl Sulfosuccinate | 397.5 | 39.75 |
| Coconut Oil | 593.8 | 59.38 |
| FD&C Yellow No 6 Lake | 8.7 | 0.87 |
| TOTAL | 1000.0 | 100.00 |

The coloured surfactant precursor having the above composition was manufactured in accordance with the above general method.

Example 2—Powdered Surfactant Composition

| Phase | Material | Weight (g) | wt. % |
|---|---|---|---|
| A | Sodium Bicarbonate | 560.0 | 56.00 |
|   | Fragrance | 20.0 | 2.00 |
| B | Coconut Oil | 130.0 | 13.00 |
|   | D&C Red 30 Lake | 1.0 | 0.10 |
|   | Disodium Laureth Sulfosuccinate | 60.0 | 6.00 |
| C | Kaolin | 50.0 | 5.00 |
|   | Citric Acid | 178.8 | 17.88 |
| D | CI42090 FD&C Blue No 1 | 0.2 | 0.02 |
|   |   | 1000.0 | 100.00 |

Method:
1. The components of Phase A were mixed together in order to disperse the fragrance.
2. In accordance with the above general method, the coconut oil of Phase B was warmed until it was in a molten state and then added to the colourant. The disodium laureth sulfosuccinate was incorporated and the resulting mixture was warmed to 75° C. in order to thoroughly dissolve the surfactant.
3. Phase A was added to Phase B and mixed together thoroughly to disperse all the components thoroughly.
4. Phase C was combined into Phases A and B and mixed for 5 minutes until all of the constituent parts were fully dispersed.
5. Phase D was thoroughly blended into the resulting mixture.
6. The resulting composition was sieved to form a loose powdered composition.

The final composition was a free-flowing powder that can be poured on to the user's skin, in a similar way as shower gel and can then be massaged into the skin, in the presences of water, to generate a foam/lather. This resulted in a thin layer of small coloured bubbles that maintained their colour intensity for a significant period of time.

As discussed herein, it has been found that when a surfactant composition comprised of a coloured surfactant composition in accordance with the present invention is combined with an additional water soluble colouring, a multicoloured surfactant composition can be formed. This resulted in the ability to colour a body of water one colour, whilst colouring the lather or foam generated by the surfactant another distinct colour.

Example 3—Solid Surfactant Composition

| Phase | Material | Weight (g) | wt. % |
|---|---|---|---|
| A | Sodium Bicarbonate | 510.0 | 51.00 |
|   | Cream of Tartar | 230.0 | 23.00 |
|   | Fragrance | 30.0 | 3.00 |
| B | Jojoba Oil | 159.3 | 15.93 |
|   | Disodium Laureth Sulfosuccinate | 69.0 | 6.90 |
|   | FD&C Red 40 Lake | 1.7 | 0.17 |
|   |   | 1000.0 | 100.00 |

Method:
1. The sodium bicarbonate and cream of tartar of Phase A were thoroughly blended together, after which the fragrances were added.
2. In accordance with the above general method, the jojoba oil of Phase B was warmed to 75° C., the colourant was dispersed throughout the warmed oil and the surfactant dissolved into the coloured oil.
3. Phase B was gradually incorporated into Phase A and mixed for 5 minutes until all of the constituent parts were fully dispersed.
4. The product was moulded to the desired shape and size and left to set at room temperature.

The product prepared was a are solid compositions that was initially pliable, enabling them to be moulded into a desired shape, before being allowed to set to a hardened surfactant product. Prior to use they are broken apart and crumbled under running water to produce large masses of coloured bubbles on the water's surface.

Example 4—Liquid Surfactant Composition

| Phase | Material | Weight (g) | wt. % |
|---|---|---|---|
| A | Olive Oil | 678.0 | 67.80 |
|   | Disodium Lauryl Sulfosuccinate | 200.0 | 20.00 |
|   | Sodium Lauryl Sulfate | 100.0 | 10.00 |
|   | FD&C Blue No 1 Lake | 2.0 | 0.20 |
|   |   | 0.0 |   |
| B | Fragrance | 20.0 | 2.00 |
|   |   | 0.0 |   |
|   |   | 1000.0 | 100.00 |

Method:
1. In accordance with the above general method, the olive oil of Phase A was warmed to 75° C. and the colourant was thoroughly incorporated. The disodium laureth sulfosuccinate and sodium lauryl sulfate were gradually added to the oil phase until they were completely dissolved.

2. The resulting composition was cooled to room temperature and blended with the fragrances.

This was a smooth liquid composition that could be readily poured from a container under a running tap, resulting in the rapid formation of large masses of coloured bubbles on the water's surface.

Example 5—Solid Bath Oil Composition

| Phase | Material | Weight (g) | wt. % |
|-------|----------|------------|-------|
| A | Cocoa Butter | 490.0 | 49.00 |
| | Almond Oil | 215.0 | 21.50 |
| | Sodium Cocoamphoacetate | 257.0 | 25.70 |
| | Ultramarine Blue | 8.0 | 0.80 |
| B | Fragrance | 30.0 | 3.00 |
| | | 1000.0 | 100.00 |

Method:
1. The cocoa butter of Phase A was warmed until it was completely molten and then added to the almond oil, whilst whisking.
2. The temperature of Phase A was raised to 75° C. and the colourant and surfactant were thoroughly incorporated.
3. Phase A was cooled to 30° C. and the fragrance of Phase B was added.
4. The resulting mixture was poured into moulds and left to completely set at room temperature.

The solid composition is capable of providing a concentrated dose of surfactant and colour to a bath. The Solid Bath Oil composition can be placed directly under a running tap, whereby the heat and the force of the running water enable the composition to melt and the surfactant to produce large masses of coloured bubbles on the water's surface.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A coloured surfactant composition consisting of:
   (i) an anhydrous surfactant present in an amount of from 25 to 70 wt. % based on the coloured surfactant composition, wherein the anhydrous surfactant is selected from the group consisting of: disodium lauryl sulfosuccinate, sodium lauryl sulphate, sodium cocoamphoacetate, sodium laureth sulphate, lauryl betaine, sodium lauroyl sarcosinate, sodium alkyl sulfate, disodium laureth sulfosuccinate, cocamide monoethanolamine, cetrimonium bromide and mixtures thereof, wherein the anhydrous surfactant comprises comprising water in an amount of less than 10 wt % based on a total amount of surfactant;
   (ii) a vegetable oil, a vegetable butter or mixture thereof present in an amount of from 25 to 75 wt. % based on the coloured surfactant composition, wherein the vegetable oil, vegetable butter or mixture thereof is selected from the group consisting of: coconut oil, almond oil, corn oil, jojoba oil, castor oil, olive oil, grape seed oil, argan oil, moringa oil, baobab oil, rose hip oil, kalahari melon oil, brazil nut oil and mixtures thereof; and
   (iii) an oil dispersible water insoluble colouring present in an amount of from 0.01 to 5 wt. % based on the coloured surfactant composition.

2. A coloured surfactant composition according to claim 1 wherein the anhydrous surfactant is present in an amount of from 45 to 60 wt. % based on the coloured surfactant composition.

3. A coloured surfactant composition according to claim 1 wherein the anhydrous surfactant is selected from the group consisting of: disodium lauryl sulfosuccinate, sodium lauryl sulphate, sodium laureth sulphate, and mixtures thereof.

4. A coloured surfactant composition according to claim 1 wherein the anhydrous surfactant is disodium lauryl sulfosuccinate.

5. A coloured surfactant composition according to claim 1 wherein the vegetable oil, vegetable butter or mixture thereof is present in an amount of from 45 to 65 wt. % based on the coloured surfactant composition.

6. A coloured surfactant composition according to claim 1 wherein the vegetable oil, vegetable butter or mixture thereof is selected from the group consisting of: coconut oil, almond oil, moringa oil, olive oil and mixtures thereof.

7. A coloured surfactant composition according to claim 1 wherein the oil dispersible water insoluble colouring is present in an amount of from 0.05 to 3 wt. % based on the coloured surfactant composition.

8. A coloured surfactant composition according to claim 1 wherein the oil dispersible water insoluble colouring is selected from the group consisting of: lake colours, inorganic pigments, inorganic dyes, water insoluble organic pigments, water insoluble organic dyes and mixtures thereof.

9. A coloured surfactant composition according to claim 1 wherein the oil dispersible water insoluble colouring is selected from the group consisting of:
   (i) a dye selected from the group consisting of FD&C Red No 2, FD&C Red No 3, FD&C Red No 40, FD&C Blue No 1, FD&C Blue No 2, FD&C Green No 3, FD&C Yellow No 5, FD&C Yellow No 6, D&C Red No 6, D&C Red No 7, D&C Red No 21, D&C Red No 22, D&C Red No 27, D&C Red No 28, D&C Red No 30, D&C Red No 33, D&C Red No 34, D&C Red No 36, D&C Yellow No 10, D&C Orange No 5 and mixtures thereof, and
   (ii) precipitated on to an inert binder selected from the group consisting of: aluminium hydroxide, aluminium (III) oxide, barium sulphate, calcium sulphate, aluminium potassium sulphate, aluminium acetate, aluminium sulfate, aluminium ammonium sulfate, copper (II) sulphate, potassium dichromate, iron (II) sulfate, sodium dithionite, tin (IV) chloride, zinc acetate and mixtures thereof.

10. A cosmetic composition comprising the coloured surfactant composition as defined in claim 1.

* * * * *